United States Patent
Noordeen et al.

(10) Patent No.: US 10,405,896 B2
(45) Date of Patent: Sep. 10, 2019

(54) ROD REDUCER

(71) Applicant: K2M, Inc., Leesburg, VA (US)

(72) Inventors: Hilali Noordeen, London (GB);
Michael Barrus, Ashburn, VA (US)

(73) Assignee: K2M, Inc., Leesburg, VA (US)

( * ) Notice: Subject to any disclaimer, the term of this patent is extended or adjusted under 35 U.S.C. 154(b) by 123 days.

(21) Appl. No.: 15/570,468

(22) PCT Filed: Oct. 1, 2015

(86) PCT No.: PCT/US2015/053386
§ 371 (c)(1),
(2) Date: Oct. 30, 2017

(87) PCT Pub. No.: WO2016/175885
PCT Pub. Date: Nov. 3, 2016

(65) Prior Publication Data
US 2018/0140337 A1    May 24, 2018

Related U.S. Application Data

(60) Provisional application No. 62/154,940, filed on Apr. 30, 2015.

(51) Int. Cl.
*A61B 17/70* (2006.01)
*A61B 17/56* (2006.01)
*A61B 17/88* (2006.01)

(52) U.S. Cl.
CPC .......... *A61B 17/7086* (2013.01); *A61B 17/56* (2013.01); *A61B 17/70* (2013.01);
(Continued)

(58) Field of Classification Search
CPC ....................................... A61B 17/7074–7091
See application file for complete search history.

(56) References Cited

U.S. PATENT DOCUMENTS

| 2,248,054 A | 7/1941 | Becker |
| 3,604,487 A | 9/1971 | Gilbert |
| (Continued) | | |

FOREIGN PATENT DOCUMENTS

FR    2985166 A1    7/2013

OTHER PUBLICATIONS

International Search Report and Written Opinion from Int'l Appl. No. PCT/US14/59425 dated Jan. 12, 2015.
(Continued)

*Primary Examiner* — Lynnsy M Summitt
(74) *Attorney, Agent, or Firm* — Lerner, David, Littenberg, Krumholz & Mentlik, LLP

(57) ABSTRACT

A rod reducer including a housing, a plurality of arm members, an anvil, a shaft, a sleeve, and a plurality of locking feet. The shaft and locking feet are coupled to the anvil. The housing is slidably disposed within a cavity of the sleeve and defines an opening to receive the shaft. The locking feet are additionally coupled to the sleeve and are pivotable between an engaged configuration with the sleeve in a distal position with respect to the anvil and a released configuration with the sleeve in a proximal position. In the engaged configuration an engagement surface of the locking feet couple to an outer housing of a dual layered housing of a bone screw such that proximal translation of the shaft drives the outer housing proximally with respect to an inner housing of the bone screw into a partially locked or locked configuration.

17 Claims, 9 Drawing Sheets

(52) U.S. Cl.
CPC .......... *A61B 17/7037* (2013.01); *A61B 17/88* (2013.01); *A61B 17/7032* (2013.01)

(56) References Cited

U.S. PATENT DOCUMENTS

| | | | |
|---|---|---|---|
| 4,263,899 A | 4/1981 | Burgin | |
| 5,020,519 A | 6/1991 | Hayes et al. | |
| 5,364,397 A | 11/1994 | Hayes et al. | |
| 5,420,751 A | 5/1995 | Burns | |
| 5,431,658 A | 7/1995 | Moskovich | |
| 5,466,243 A | 11/1995 | Schmieding et al. | |
| 5,529,571 A | 6/1996 | Daniel | |
| 5,685,826 A | 11/1997 | Bonutti | |
| 5,720,751 A | 2/1998 | Jackson | |
| 5,910,141 A | 6/1999 | Morrison et al. | |
| 5,944,658 A | 8/1999 | Koros et al. | |
| 5,951,564 A | 9/1999 | Schroder et al. | |
| 6,123,707 A | 9/2000 | Wagner | |
| 6,200,322 B1 | 3/2001 | Branch et al. | |
| 6,416,521 B1 | 7/2002 | Waldner et al. | |
| 6,440,133 B1 | 8/2002 | Beale et al. | |
| 6,488,682 B2 | 12/2002 | Kikuchi et al. | |
| 6,616,605 B2 | 9/2003 | Wright et al. | |
| 6,648,888 B1 | 11/2003 | Shluzas | |
| 6,660,006 B2 | 12/2003 | Markworth et al. | |
| 6,743,231 B1 | 6/2004 | Gray et al. | |
| 6,746,449 B2 | 6/2004 | Jones et al. | |
| 6,790,208 B2 | 9/2004 | Oribe et al. | |
| 6,790,209 B2 | 9/2004 | Beale et al. | |
| 6,849,064 B2 | 2/2005 | Hamada | |
| 6,923,814 B1 | 8/2005 | Hildebrand et al. | |
| 6,929,606 B2 | 8/2005 | Ritland | |
| 6,932,822 B2 | 8/2005 | Oribe et al. | |
| 6,957,758 B2 | 10/2005 | Aranyi | |
| 7,008,422 B2 | 3/2006 | Foley et al. | |
| 7,011,660 B2 | 3/2006 | Sherman et al. | |
| 7,083,621 B2 | 8/2006 | Shaolian et al. | |
| 7,156,849 B2 | 1/2007 | Dunbar et al. | |
| 7,160,300 B2 | 1/2007 | Jackson | |
| 7,179,261 B2 | 2/2007 | Sicvol et al. | |
| 7,188,626 B2 | 3/2007 | Foley et al. | |
| 7,226,453 B2 | 6/2007 | Chao et al. | |
| 7,250,052 B2 | 7/2007 | Landry et al. | |
| 7,371,239 B2 | 5/2008 | Dec et al. | |
| 7,462,182 B2 | 12/2008 | Lim | |
| 7,473,267 B2 | 1/2009 | Nguyen et al. | |
| 7,481,813 B1 | 1/2009 | Purcell | |
| 7,491,207 B2 | 2/2009 | Keyer et al. | |
| 7,491,208 B2 | 2/2009 | Pond, Jr. et al. | |
| 7,497,869 B2 | 3/2009 | Justis | |
| 7,520,879 B2 | 4/2009 | Justis et al. | |
| 7,547,318 B2 | 6/2009 | Birkmeyer et al. | |
| 7,563,264 B2 | 7/2009 | Landry et al. | |
| 7,572,264 B2 | 8/2009 | Null et al. | |
| 7,575,581 B2 | 8/2009 | Lovell | |
| 7,588,575 B2 | 9/2009 | Colleran et al. | |
| 7,588,588 B2 | 9/2009 | Spitler et al. | |
| 7,591,836 B2 | 9/2009 | Dick et al. | |
| 7,597,694 B2 * | 10/2009 | Lim | A61B 17/7005 606/86 A |
| 7,608,081 B2 | 10/2009 | Abdelgany | |
| 7,611,517 B2 | 11/2009 | Lim | |
| 7,618,442 B2 | 11/2009 | Spitler et al. | |
| 7,621,918 B2 | 11/2009 | Jackson | |
| 7,625,379 B2 | 12/2009 | Puno et al. | |
| 7,637,914 B2 | 12/2009 | Stern | |
| 7,651,502 B2 | 1/2010 | Jackson | |
| 7,655,008 B2 | 2/2010 | Lenke et al. | |
| 7,666,189 B2 | 2/2010 | Gerber et al. | |
| 7,691,132 B2 | 4/2010 | Landry et al. | |
| 7,708,763 B2 | 5/2010 | Selover et al. | |
| 7,776,040 B2 | 8/2010 | Markworth et al. | |
| 7,815,664 B2 * | 10/2010 | Sherman | A61B 17/7031 606/250 |
| 7,824,411 B2 * | 11/2010 | Varieur | A61B 17/7091 606/86 A |
| 7,842,044 B2 * | 11/2010 | Runco | A61B 17/7076 606/104 |
| 7,854,751 B2 | 12/2010 | Sicvol et al. | |
| 7,887,541 B2 | 2/2011 | Runco et al. | |
| 7,909,835 B2 | 3/2011 | Oribe et al. | |
| 7,922,749 B2 | 4/2011 | Dewey | |
| 7,927,334 B2 | 4/2011 | Miller et al. | |
| 7,931,654 B2 * | 4/2011 | Jones | A61B 17/7091 606/86 A |
| 7,946,982 B2 | 5/2011 | Hamada | |
| 7,955,355 B2 | 6/2011 | Chin | |
| 7,988,694 B2 | 8/2011 | Barrus et al. | |
| 8,002,798 B2 | 8/2011 | Chin et al. | |
| 8,128,629 B2 * | 3/2012 | Barry | A61B 17/7086 606/205 |
| 8,137,357 B2 * | 3/2012 | Barry | A61B 17/7074 606/205 |
| 8,147,524 B2 | 4/2012 | Vallespir | |
| 8,192,438 B2 | 6/2012 | Garamszegi | |
| 8,230,863 B2 | 7/2012 | Ravikumar et al. | |
| 8,235,997 B2 * | 8/2012 | Hoffman | A61B 17/7086 606/53 |
| 8,246,623 B2 * | 8/2012 | Peultier | A61B 17/7088 606/246 |
| 8,298,138 B2 | 10/2012 | Gorek et al. | |
| 8,303,595 B2 | 11/2012 | Jones | |
| 8,308,729 B2 * | 11/2012 | Nunley | A61B 17/7086 606/86 A |
| 8,308,774 B2 * | 11/2012 | Hoffman | A61B 17/7091 606/279 |
| 8,323,286 B2 * | 12/2012 | Justis | A61B 17/708 606/86 A |
| 8,361,122 B2 | 1/2013 | Barrus et al. | |
| 8,672,944 B2 * | 3/2014 | Boachie-Adjei | A61B 17/708 606/246 |
| 8,828,006 B2 * | 9/2014 | Semler | A61B 17/708 606/305 |
| 8,936,606 B2 * | 1/2015 | Gleason | A61B 17/88 606/104 |
| 8,961,523 B2 * | 2/2015 | Barrus | A61B 17/7086 606/86 A |
| 8,986,319 B2 * | 3/2015 | Smith | A61B 17/7076 606/104 |
| 9,050,143 B2 * | 6/2015 | May | A61B 17/7043 |
| 9,066,758 B2 * | 6/2015 | Justis | A61B 17/7082 |
| 9,078,709 B2 * | 7/2015 | McBride | A61B 17/7076 |
| 9,125,703 B2 * | 9/2015 | McClintock | A61B 17/88 |
| 9,204,909 B2 * | 12/2015 | Rezach | A61B 17/7076 |
| 9,216,043 B2 * | 12/2015 | Stad | A61B 17/7076 |
| 9,271,768 B2 * | 3/2016 | Artaki | A61B 17/7002 |
| 9,451,998 B2 * | 9/2016 | McBride | A61B 17/7085 |
| 9,452,000 B2 * | 9/2016 | Barrus | A61B 17/7086 |
| 9,561,062 B2 * | 2/2017 | Hayes | A61B 17/025 |
| 9,655,653 B2 * | 5/2017 | Lindner | A61B 17/7032 |
| 9,668,789 B2 * | 6/2017 | Barrett | A61B 17/708 |
| 9,743,958 B2 * | 8/2017 | Ishii | A61B 17/7032 |
| 9,918,752 B2 * | 3/2018 | Hennard | A61B 17/7086 |
| 9,918,753 B2 * | 3/2018 | May | A61B 17/7086 |
| 9,943,344 B2 * | 4/2018 | Mladenov | A61B 17/7002 |
| 10,117,678 B2 * | 11/2018 | Angus | A61B 17/7032 |
| 10,166,050 B2 * | 1/2019 | Heuer | A61B 17/7082 |
| 2002/0052603 A1 | 5/2002 | Nichols et al. | |
| 2003/0225408 A1 | 12/2003 | Nichols et al. | |
| 2004/0215190 A1 | 10/2004 | Nguyen et al. | |
| 2004/0230191 A1 | 11/2004 | Frey et al. | |
| 2004/0267275 A1 | 12/2004 | Cournoyer et al. | |
| 2005/0059969 A1 | 3/2005 | McKinley | |
| 2005/0143749 A1 | 6/2005 | Zalenski et al. | |
| 2005/0149053 A1 | 7/2005 | Varieur et al. | |
| 2005/0192587 A1 | 9/2005 | Lim | |
| 2005/0192589 A1 | 9/2005 | Raymond et al. | |
| 2005/0261702 A1 | 11/2005 | Oribe et al. | |
| 2005/0277934 A1 | 12/2005 | Vardiman | |
| 2006/0025769 A1 | 2/2006 | Dick et al. | |
| 2006/0036260 A1 | 2/2006 | Runco et al. | |
| 2006/0074418 A1 | 4/2006 | Jackson | |

(56) References Cited

U.S. PATENT DOCUMENTS

| | | | |
|---|---|---|---|
| 2006/0089651 A1* | 4/2006 | Trudeau | A61B 17/7086 606/86 R |
| 2006/0200132 A1 | 9/2006 | Chao et al. | |
| 2006/0271050 A1 | 11/2006 | Vallespir | |
| 2007/0016193 A1 | 1/2007 | Ritland | |
| 2007/0055247 A1 | 3/2007 | Jahng | |
| 2007/0093817 A1 | 4/2007 | Barrus et al. | |
| 2007/0213716 A1 | 9/2007 | Lenke et al. | |
| 2007/0213722 A1 | 9/2007 | Jones et al. | |
| 2007/0270811 A1 | 11/2007 | Dewey | |
| 2007/0270867 A1 | 11/2007 | Miller et al. | |
| 2007/0276379 A1 | 11/2007 | Miller et al. | |
| 2007/0282337 A1 | 12/2007 | Garamszegi | |
| 2008/0015601 A1 | 1/2008 | Castro et al. | |
| 2008/0154277 A1* | 6/2008 | Machalk | A61B 17/7091 606/99 |
| 2008/0172062 A1 | 7/2008 | Donahue et al. | |
| 2009/0018593 A1 | 1/2009 | Barrus et al. | |
| 2010/0036434 A1* | 2/2010 | Ely | A61B 17/7091 606/305 |
| 2011/0054259 A1 | 3/2011 | Gorek et al. | |
| 2011/0118791 A1 | 5/2011 | Nunley et al. | |
| 2011/0172714 A1 | 7/2011 | Boachie-Adjei et al. | |
| 2012/0016424 A1* | 1/2012 | Kave | A61B 17/7037 606/305 |
| 2012/0083853 A1 | 4/2012 | Boachie-Adjei et al. | |
| 2012/0109208 A1* | 5/2012 | Justis | A61B 17/7032 606/264 |
| 2012/0191144 A1* | 7/2012 | Peultier | A61B 17/7086 606/86 A |
| 2012/0277808 A1* | 11/2012 | May | A61B 17/7086 606/86 A |
| 2013/0041228 A1 | 2/2013 | Gorek et al. | |
| 2013/0046344 A1 | 2/2013 | Nunley et al. | |
| 2014/0163617 A1 | 6/2014 | Boachie-Adjei et al. | |
| 2015/0066042 A1 | 3/2015 | Cummins et al. | |
| 2015/0100097 A1 | 4/2015 | Barrus | |
| 2015/0100098 A1* | 4/2015 | Moore | A61B 17/7086 606/86 A |
| 2017/0224384 A1* | 8/2017 | Barrus | A61B 17/7001 |
| 2018/0140336 A1* | 5/2018 | Garcia-Bengochea | A61B 17/7002 |
| 2018/0199964 A1* | 7/2018 | Min | A61B 17/7086 |
| 2019/0029730 A1* | 1/2019 | Angus | A61B 17/7032 |

OTHER PUBLICATIONS

European Search Report issued in EP16151523.4 dated Jun. 23, 2016.

International Preliminary Report and Written Opinion issued in corresponding International Application No. PCT/US2015/053386 dated Nov. 9, 2017.

\* cited by examiner

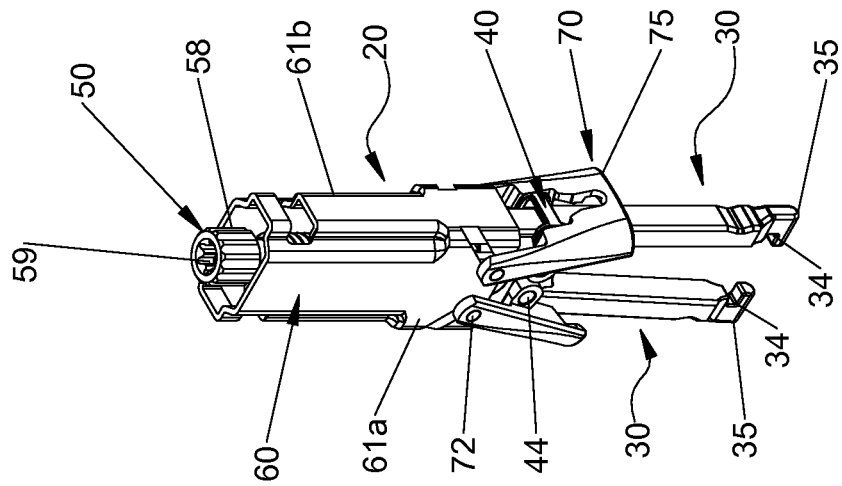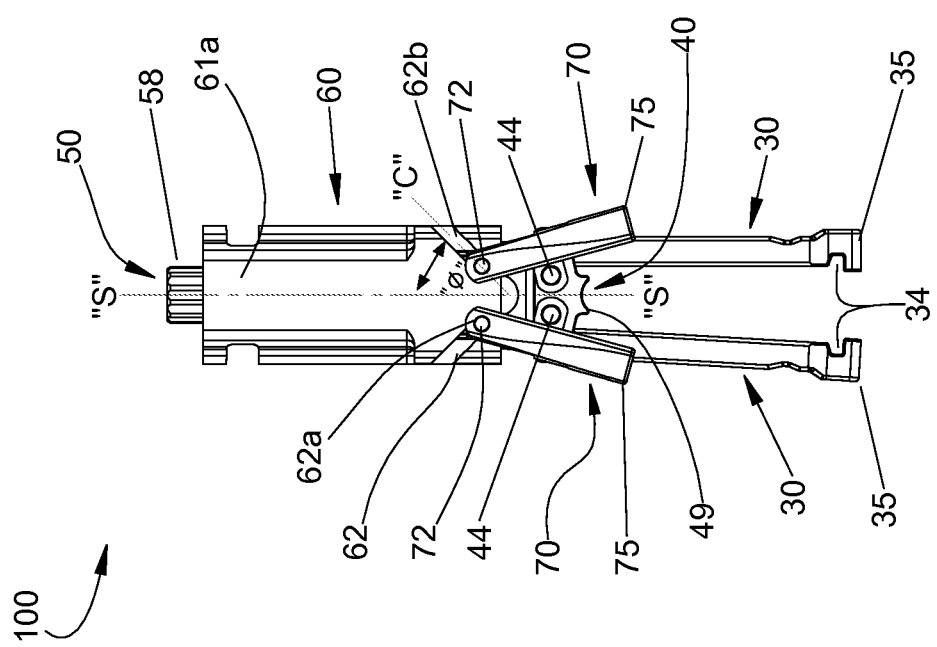

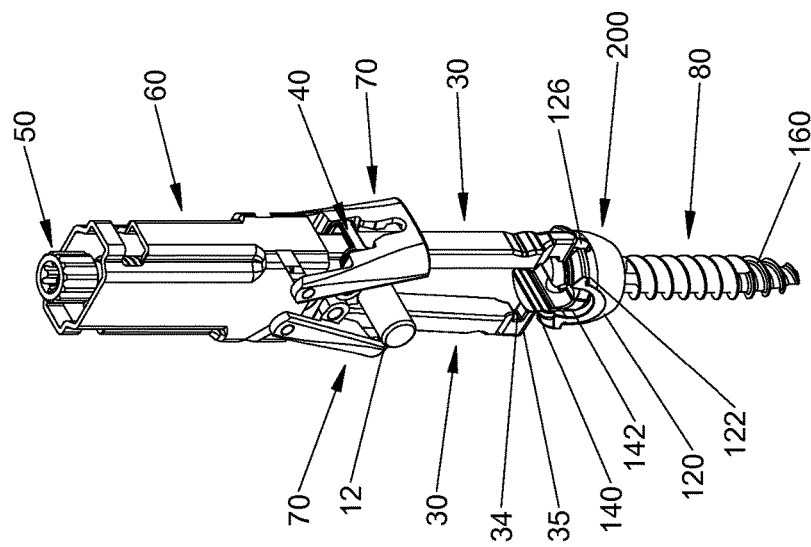
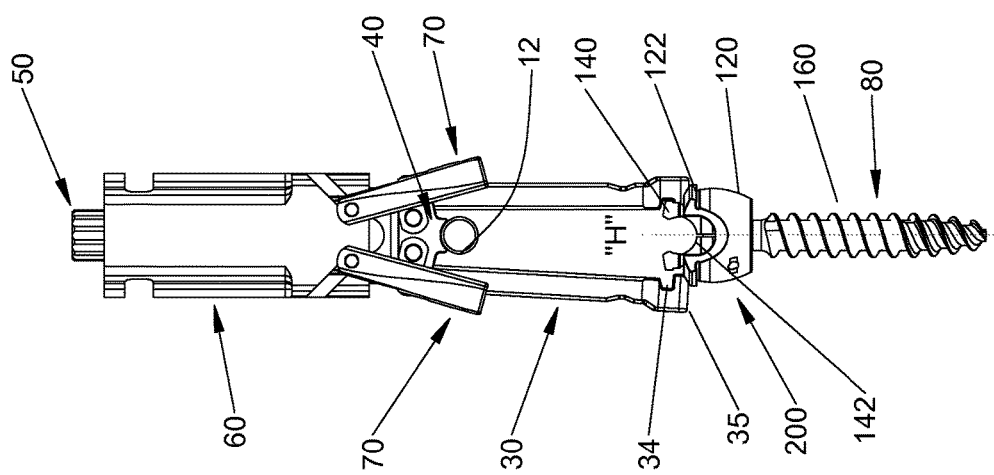
FIG. 6B
FIG. 6A

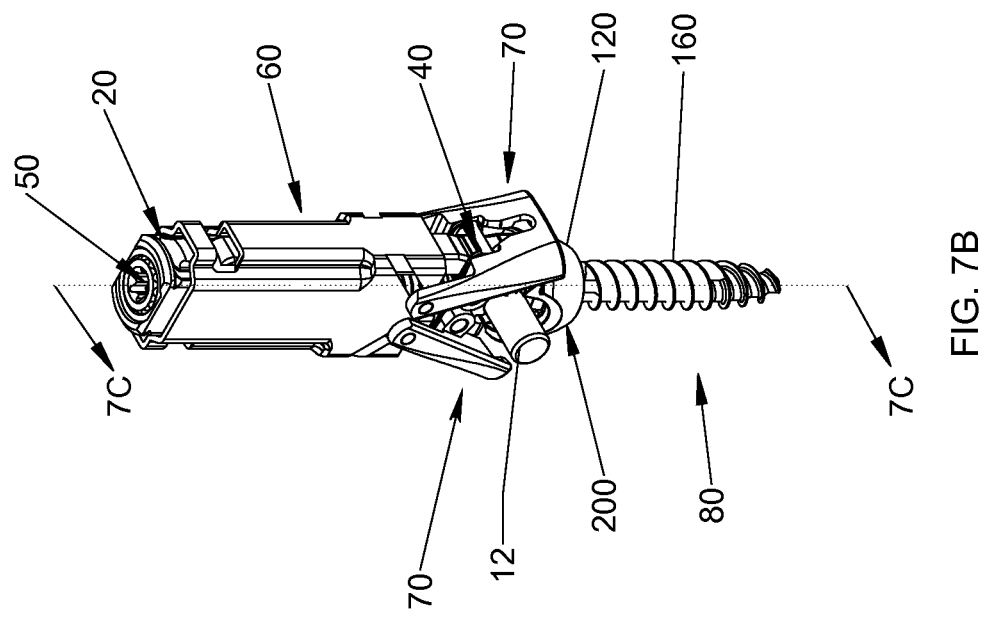
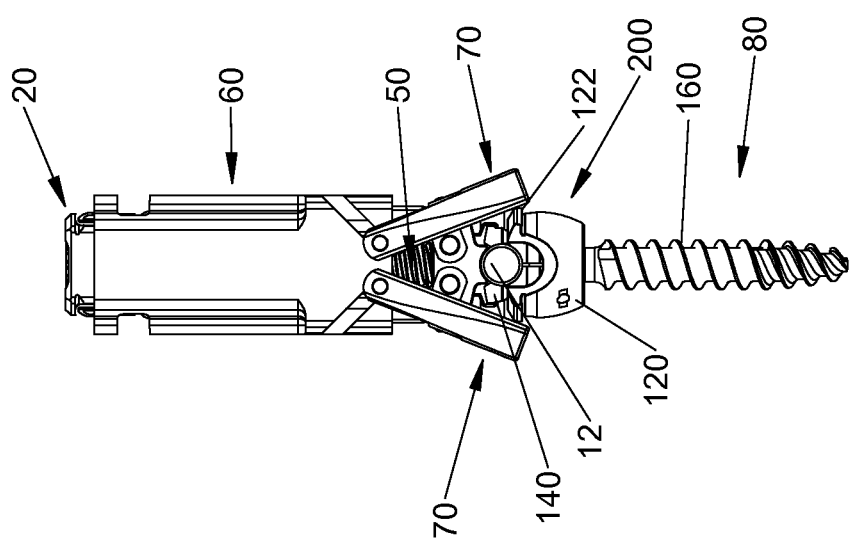
FIG. 7B
FIG. 7A

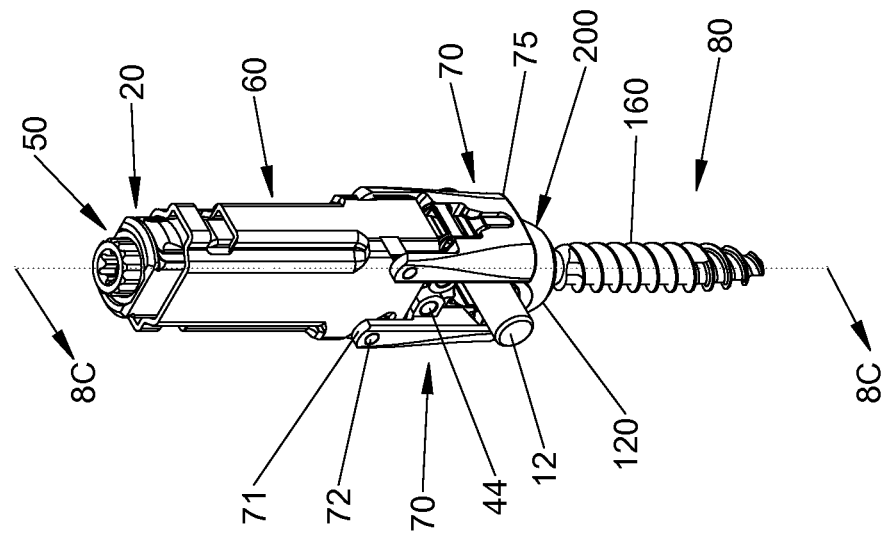
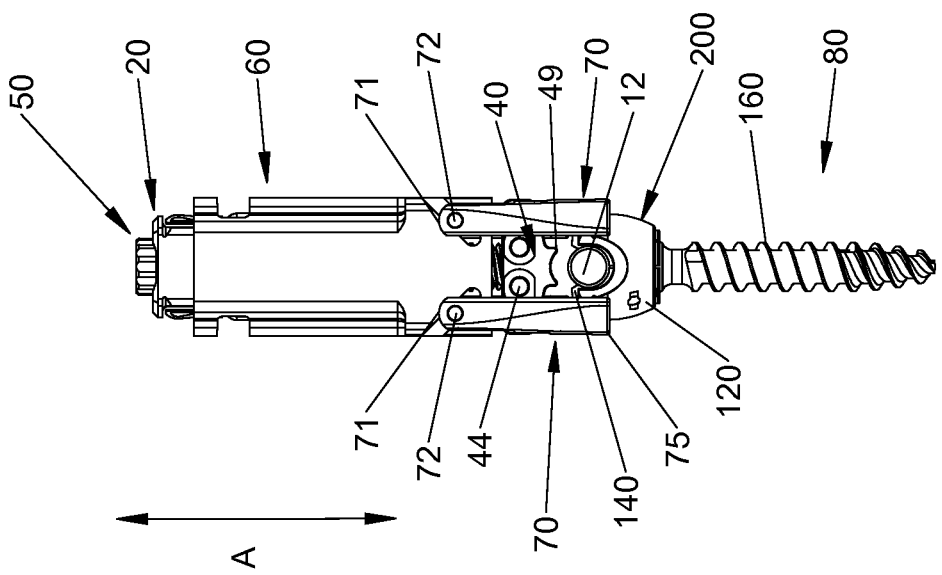
FIG. 8B
FIG. 8A

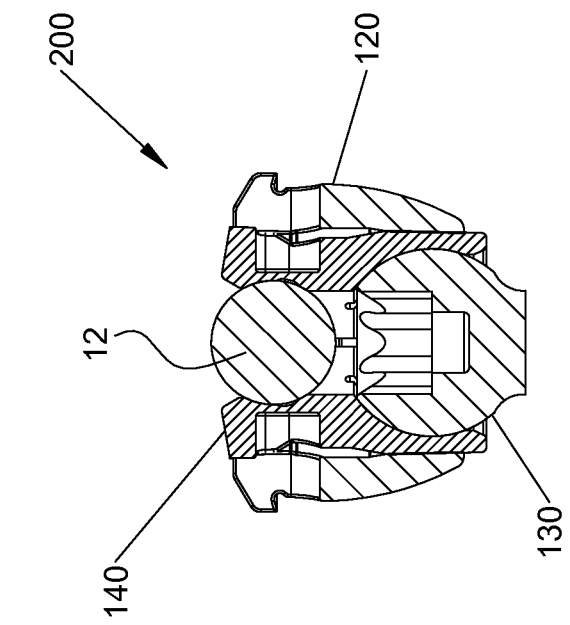
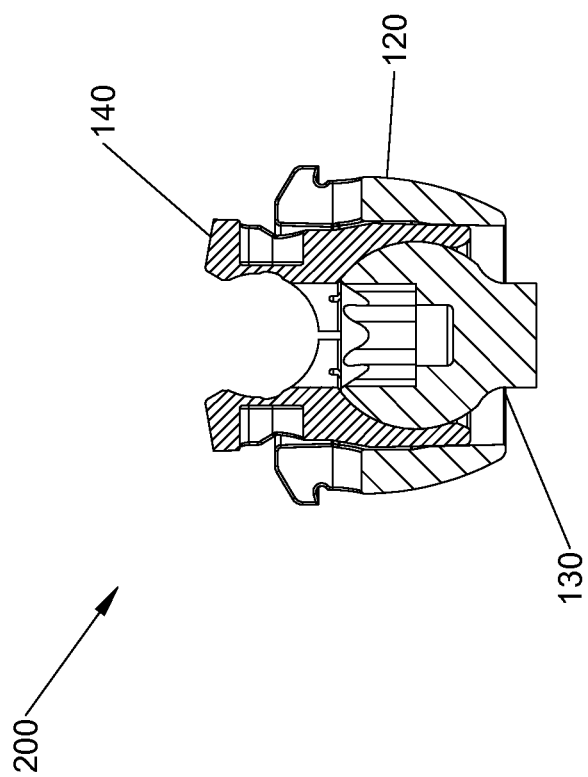

ROD REDUCER

CROSS-REFERENCE TO RELATED APPLICATION

This application claims the benefit of and priority to U.S. Provisional Application No. 62/154,940 filed Apr. 30, 2015, the entire content of which is incorporated herein by reference.

BACKGROUND

Technical Field

The present disclosure relates to an orthopedic apparatus for stabilizing and fixing the bones and joints of the body. Particularly, the present disclosure relates to a manually operated apparatus for reducing and securing a spinal rod into a bone screw.

Description of Related Art

The spinal column is a complex system of bones and connective tissues that provides support for the human body and protection for the spinal cord and nerves. The human spine is comprised of thirty-three vertebrae at birth and twenty-four as a mature adult. Between each pair of vertebrae is an intervertebral disc, which maintains the space between adjacent vertebrae and acts as a cushion under compressive, bending, and rotational loads and motions.

There are various disorders, diseases, and types of injury that the spinal column may experience in a lifetime. The problems may include but are not limited to scoliosis, kyphosis, excessive lordosis, spondylolisthesis, slipped or ruptured disc, degenerative disc disease, vertebral body fracture, and tumors. Persons suffering from any of the above conditions typically experience extreme or debilitating pain and often times diminished nerve function.

One of the more common solutions to any of the above mentioned conditions involves a surgical procedure known as spinal fusion. A spinal fusion procedure involves fusing two or more vertebral bodies in order to stabilize or eliminate motion at the intervertebral disc or joint. To achieve this, natural or artificial bone, along with a spacing device, replaces either part, or all of the intervertebral disc to form a rigid column of bone, which is stabilized by mechanical hardware.

The mechanical hardware used to immobilize the spinal column typically involves rods or plates that are secured to a plurality of vertebrae using a series of bone pins, bone screws, bone hooks, or other suitable bone anchors. When the spine surgery is performed posteriorly, it is common practice to place screws into the vertebral bodies and then connect a metal rod between adjacent vertebral bodies. When the spine surgery is performed anteriorly, it is common practice to attach a thin metal plate directly to the vertebral bodies and secure it to each vertebral level using one or more bone screws.

Coupling a spinal rod with a bone screw may involve the use of a number of discrete tools. Typically, a rod reducer is employed to seat the spinal rod in a housing of the bone screw and, after the rod reducer is disconnected from the bone screw, a locking instrument is used to lock the spinal rod in the bone screw by either inserting and seating a set-screw for set-screw style bone screws or transitioning the outer housing relative to the inner housing for taper lock style bone screws. It would be advantageous to provide an apparatus that is capable of reducing a rod into a bone screw and subsequently locking the bone screw.

SUMMARY

In an embodiment of the present disclosure, a surgical apparatus includes a bone screw and a rod reducer. The bone screw has inner and outer housings movable relative to each other between partially locked and unlocked configurations. The rod reducer includes a sleeve having a housing slidably disposed therein and a shaft disposed through a longitudinal opening of the housing. An anvil of the rod reducer is coupled to a distal end of the shaft. Rotation of the shaft in a first direction translates the anvil proximally relative to the housing and rotation of the shaft in a second direction translates the anvil distally relative to the housing. First and second arm members of the rod reducer are operatively coupled to the anvil and the housing. The first and second arm members being pivotable relative to the housing with the anvil in a proximal position, while the first and second arm members are in a parallel arrangement with the anvil in a distal position. First and second locking feet are slidably coupled, at proximal ends thereof, to the sleeve and pivotably coupled with the anvil, such that the first and second locking feet pivot between a released configuration and an engaged configuration. Proximal translation of the sleeve, with respect to the anvil, pivots the first and second locking feet towards the released configuration, and distal translation of the sleeve, with respect to the anvil, pivots the first and second locking feet towards the engaged configuration such that the first and second locking feet pivot towards a parallel relationship.

The bone screw may include a head and a shank and the head may be disposed in the inner housing such that the shank is rotatable and pivotable relative to the inner housing.

Pins may couple the first and second locking feet to cam slots of the sleeve, such that the pins move towards first ends of the cam slots in the released configuration and the pins move towards second ends of the cam slots in the engaged configuration.

Proximal translation of the sleeve may slide the pins towards the first ends of the cam slots. Distal translation of the sleeve may slide the pins towards the second ends of the cam slots.

The distal ends of the first and second locking feet may be configured to engage with an annular flange extending from a proximal end of the outer housing.

The proximal translation of the sleeve may pivot the first and second locking feet towards the released configuration. The first and second locking feet may define an acute angle with respect to a longitudinal axis of the shaft in the released configuration.

A method of reducing a spinal rod is also disclosed and includes coupling a first arm member and a second arm member of a rod reducer with an inner housing of a bone screw. The first and second arm members are pivotably coupled to a housing of the rod reducer. The method also includes positioning a spinal rod between an anvil of the rod reducer and the inner housing, translating a sleeve of the rod reducer distally with respect to the anvil such that locking feet pivotably coupled to the anvil and slidably coupled to the sleeve transition towards a parallel orientation with respect to each other, coupling a distal end of each locking foot to an outer housing of the bone screw, and translating the anvil and the locking feet proximally with respect to the housing such that the bone screw transitions from an unlocked configuration to a partially locked configuration.

Translating an anvil distally may include rotating a shaft coupled to the anvil in a first direction and translating an anvil proximally may include rotating the shaft in a second direction. Translating the sleeve distally may further include sliding pins disposed within cam slots of the sleeve from first ends of the cam slots towards second ends of the cam slots such that the locking feet are in the parallel orientation when the pins are approximated to the second ends of the cam slots.

The method may also include translating the sleeve proximally with respect to the anvil such that distal ends of the locking feet pivot away from one another into a spaced apart orientation, decoupling the locking feet from the outer housing of the bone screw, translating the anvil proximally, and decoupling the first and second arm members from the inner housing of the bone screw.

Translating the anvil proximally may include rotating a shaft coupled to the anvil in a first direction and translating the anvil distally may include rotating the shaft in a second direction.

A kit in accordance with the present disclosure includes at least one rod reducer, at least one bone screw, and at least one spinal rod. The at least one rod reducer includes a housing slidably disposed in a sleeve, a shaft disposed in a throughhole of the housing and coupled to an anvil, locking feet pivotably coupled to the anvil and slidably coupled to the sleeve, the locking feet attachable to an outer housing of a bone screw in a released configuration and securely attached to the outer housing in an engaged configuration, and first and second arm members pivotably coupled to the housing and configured to engage an inner housing of the bone screw, wherein distal translation of the sleeve with respect to the anvil pivots the locking feet towards the engaged configuration.

A rod reducer in accordance with the present disclosure includes a sleeve having a housing slidably disposed therein and a shaft disposed through a longitudinal opening of the housing. An anvil of the rod reducer is coupled to a distal end of the shaft. The shaft is rotatable in a first direction to translate the anvil proximally relative to the housing, and the shaft is rotatable in a second direction to translate the anvil distally relative to the housing. First and second arm members of the rod reducer are operatively coupled to the anvil and the housing. The first and second arm members being pivotable relative to the housing with the anvil in a proximal position, while the first and second arm members are parallel to each other with the anvil in a distal position. First and second locking feet are slidably coupled, at proximal ends thereof, to the sleeve and pivotably coupled with the anvil, such that the first and second locking feet pivot between a released configuration and an engaged configuration. Proximal translation of the sleeve, with respect to the anvil, pivots the first and second locking feet towards the released configuration, and distal translation of the sleeve, with respect to the anvil, pivots the first and second locking feet towards the engaged configuration such that the first and second locking feet pivot towards a parallel relationship.

BRIEF DESCRIPTION OF THE DRAWINGS

The above and other aspects and features of the present disclosure will become more apparent in light of the following detailed description when taken in conjunction with the accompanying drawings in which:

FIG. 1 is a front view of one embodiment of a rod reducer in accordance with the present disclosure;

FIG. 2 is a front perspective view of the rod reducer of FIG. 1;

FIG. 6A is a front view of the rod reducer of FIG. 1 with a bone screw in an unlocked configuration and a spinal rod prior to reducing the spinal rod therein;

FIG. 6B is a front perspective view of the rod reducer of FIG. 6A;

FIG. 7A is a front view of the rod reducer of FIG. 6A after reducing the spinal rod into the bone screw;

FIG. 7B is a front perspective view of the rod reducer of FIG.7A;

FIG. 8A is a front view of the rod reducer of FIG. 6A with a locking member of the rod reducer coupled to the bone screw after reducing the spinal rod therein and locking the bone screw;

FIG. 8B is a front perspective view of the rod reducer of FIG. 8A;

FIG. 10A is a cross-sectional view of a portion of the bone screw of FIG. 6A in an unlocked configuration; and FIG. 10B is a cross-section view of a portion of the bone screw of FIG. 6A in a locked configuration.

DETAILED DESCRIPTION OF EMBODIMENTS

Figure 4:
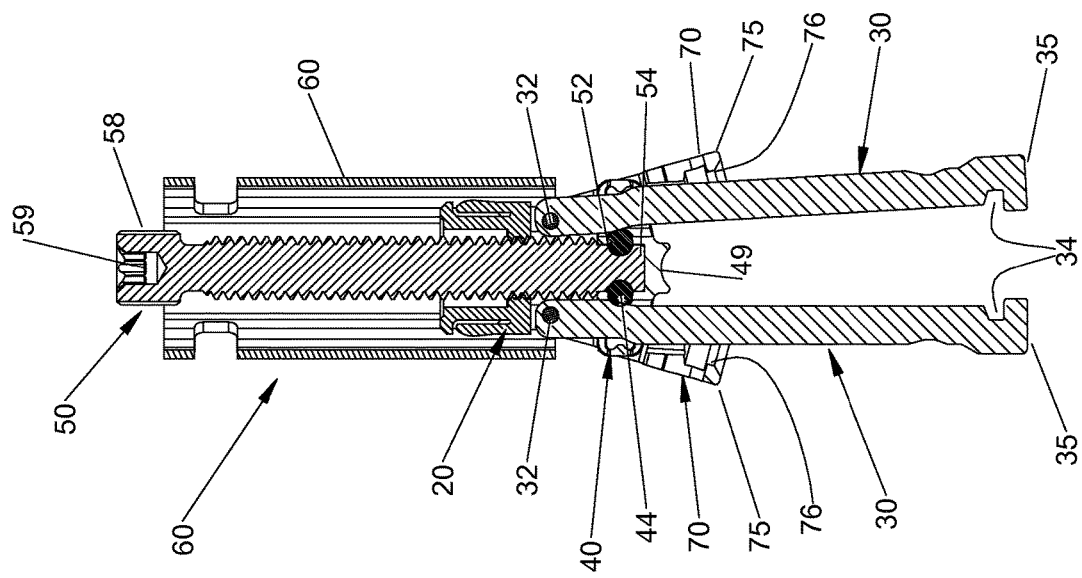
FIG. 4 is a front cross-sectional view taken along section-line 4-4 of FIG. 3.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. As understood in the art, the term "proximal" refers to the portion of the apparatus or component thereof that is closer to the clinician and the term "distal" refers to the portion of the apparatus or component thereof that is farther from the clinician. In addition, it is understood in the art that the term "cephalad" refers to a direction toward a patient's head, whereas the term "caudad" refers to a direction toward the patient's feet. Further still, it is understood in the art that the term "lateral" refers to a direction toward a side of the body of the patient, i.e., away from the middle of the body of the patient, whereas "medial" refers to a position toward the middle of the body of the patient. It is understood in the art that the term "posterior" refers to a direction toward the patient's back, and the term "anterior" refers to a direction toward the patient's front. Additionally, in the drawings and in the description that follows, terms such as front, rear, upper, lower, top, bottom, and similar directional terms are used simply for convenience of description and are not intended to limit the disclosure.

Figure 5:
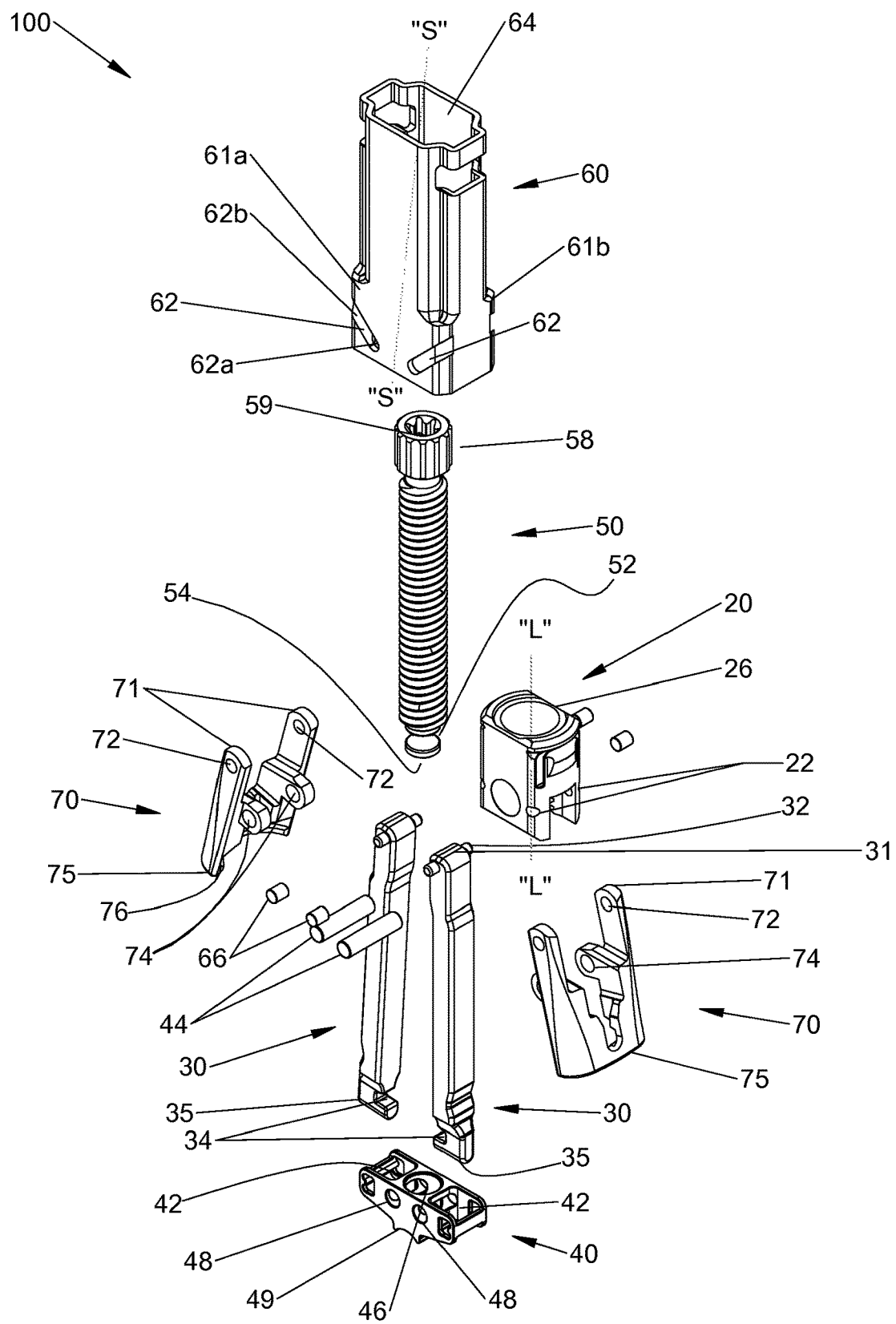
FIG. 5 is a front perspective view, with parts separated, of the rod reducer of FIG. 1.
Figure 7C:
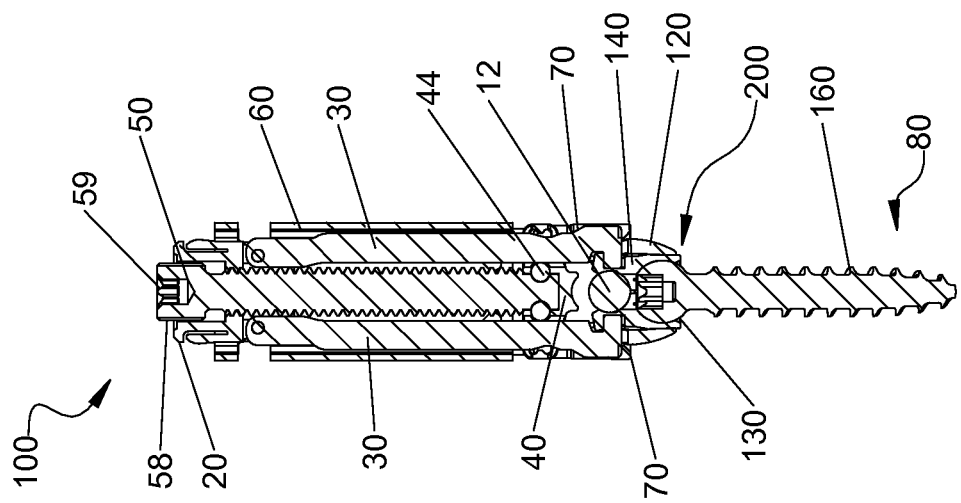
FIG. 7C is a cross-sectional view taken along section line 7C-7C of FIG. 7B.

Referring initially to FIGS. 1 and 5, a rod reducer in accordance with the present disclosure is generally designated as 100. Rod reducer 100 includes a housing 20, an arm member 30, an anvil 40, a shaft 50, a sleeve 60, and a locking foot 70. As illustrated, rod reducer 100 may include two arm members 30 and two locking feet 70. Rod reducer 100 is configured to couple with a dual layered housing 200 of a bone screw 80 and reduce a spinal rod 12 into a slot 142 defined within an inner housing 140 of dual layered housing 200 (FIG. 6A). Rod reducer 100 is further configured to transition dual layered housing 200 of bone screw 80 from an unlocked configuration (FIG. 10A) into a partially locked configuration or a locked configuration (FIG. 10B). Although the present disclosure discusses the rod reducer 100 with respect to bone screw 80, the presently disclosed rod reducer is usable with a bone pin having an unthreaded shaft and a taper lock style housing.

Figure 9:
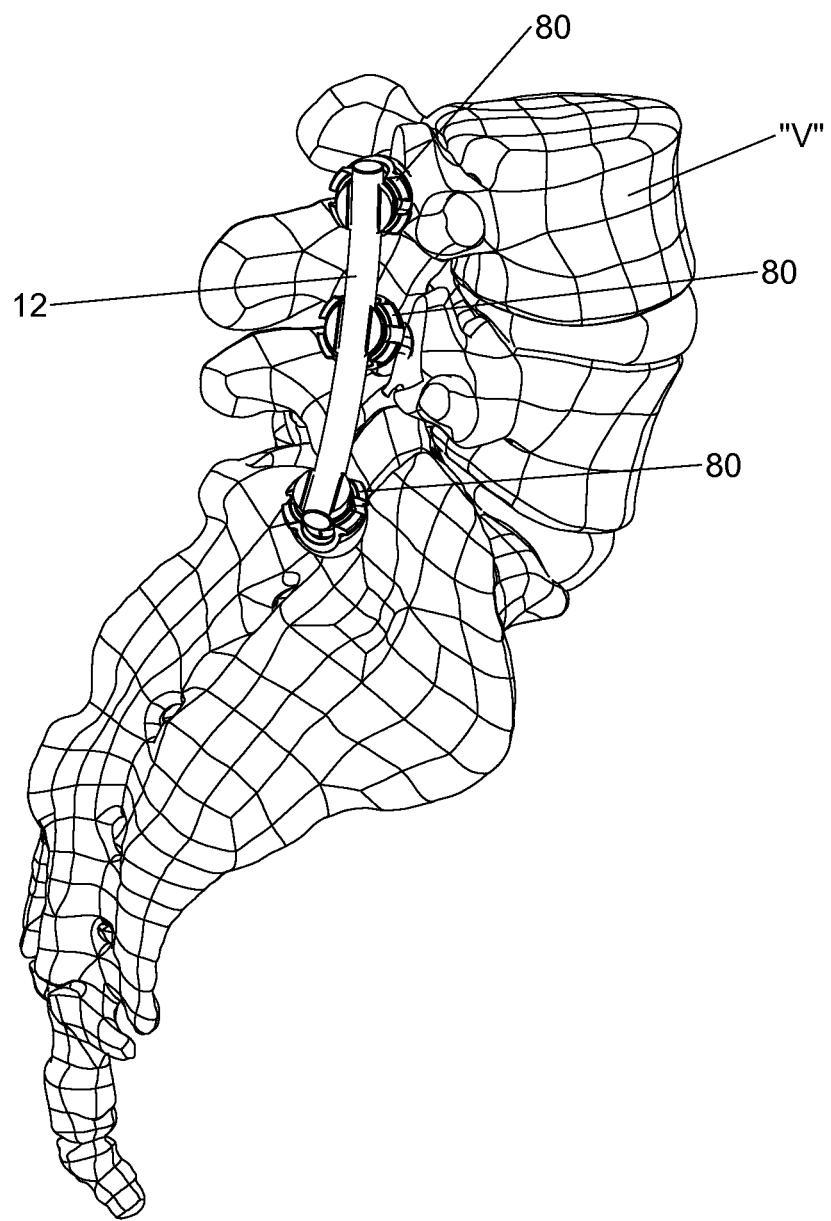
FIG. 9 is a perspective view of a spinal rod and bone screw construct coupled to a spine.

With additional reference to FIGS. 6A and 6B, dual layered housing 200 includes an outer housing 120 and an inner housing 140. It should be appreciated that bone screw 80 is a taper lock style screw where dual layered housing 200 provides a taper lock configuration. In this configuration, at least a portion of an inner surface of outer housing 120 is capable of sliding over a portion of an outer surface of inner housing 140 in upward (i.e., proximal) and downward (i.e., distal) directions along a longitudinal axis "H" of dual layered housing 200. Bone screw 80 includes a threaded shaft 160 (FIG. 6A) extending distally from dual layered housing 200. Threaded shaft 160 includes threads thereon for securing the bone screw 80 into a vertebral body "V" (FIG. 9). A screw head 130 (FIG. 10A) of bone screw 80 is rotatably, and pivotably, coupled to inner housing 140, such that dual layered housing 200 is rotatable about, and pivotably with respect to, a longitudinal axis of the threaded shaft 160. Likewise, threaded shaft 160 is rotatable and pivotable with respect to inner housing 140.

It is envisioned that rod reducer 100 may be used to insert and reduce spinal rod 12 securely within dual layered housing 200, and further, transition dual layered housing 200 from the unlocked configuration (FIG. 10A) to the locked configuration (FIG. 10B), or a partially locked configuration between the unlocked and locked configurations. In an unlocked configuration of dual layered housing 200, spinal rod 12 may be freely inserted and removed therefrom, and dual layered housing 200 may freely rotate about screw head 130 or pivot off of the longitudinal axis "H" of the threaded shaft 160. It follows that rotation about screw head 130 includes rotation about the longitudinal axis "H" of the threaded shaft 160. Similarly, threaded shaft 160 may be pivoted or rotated with respect to dual layered housing 200. In a locked configuration of dual layered housing 200, spinal rod 12 is securely fixed therein, and dual layered housing 200 is inhibited from rotating or pivoting relative to threaded shaft 160. This locked configuration also inhibits threaded shaft 160 from rotating or pivoting with respect to dual layered housing 200. In the partially locked configuration, spinal rod 12 is retained in dual layered housing 200 such that the spinal rod 12 is slidable along, and rotatable about, an axis which is transverse to the longitudinal axis "H" of dual layered housing 200 (FIG. 6A), but is inhibited from movement in a direction along longitudinal axis "H" (i.e., spinal rod 12 cannot move proximally along longitudinal axis "H"). Additionally, dual layered housing 200 and threaded shaft 160 remain rotationally and pivotally movable with respect to each other as in the unlocked configuration of the dual layered housing 200. This arrangement permits fine adjustments to be performed.

By using rod reducer 100, outer housing 120 may be driven upwards along longitudinal axis "H" with respect to inner housing 140, thereby transitioning dual layered housing 200 from the unlocked configuration (FIG. 10A) to the locked configuration (FIG. 10B.) or the partially locked configuration. The rod reducer 100 may be selectively connected to bone screw 80 and utilized to position the outer housing 120 along an outer surface of the inner housing 140 such that a compressive force exerted by the outer housing 120 upon the inner housing 140 transitions the dual layered housing 200 into the partially locked or locked configuration. Outer housing 120 may include a receiving element configured to facilitate grasping thereof by rod reducer 100. The receiving element may be a proximally located annular ridge, lip, or flange 122 extending radially from an upper portion of an outer surface of outer housing 120. Locked, unlocked, and partially locked configurations of dual layered housing 200 are shown and described in U.S. Pat. No. 8,361,122, which is hereby incorporated by reference in its entirety.

In the partially locked configuration the outer housing 120 is positioned between the unlocked configuration (FIG. 10A) and the locked configuration (FIG. 10B). With a limited amount of sliding movement of the outer housing 120 relative to the inner housing 140, partial compressive pressure will be exerted on an articulation recess defined within dual layered housing 200 and the screw head 130 positioned therein (FIG. 10A), as well as on slot 142 of the inner housing 140 and the spinal rod 12 positioned therein. The partial compressive pressure of the partially locked configuration allows the dual layered housing 200 to be repositioned with respect to the screw head 130, as well as adjustment of the spinal rod 12 with respect to the slot 142 (i.e., transverse movement relative to axis "H"). More specifically, in the partially locked configuration the dual layered housing 200 is permitted to rotate about the screw head 130 and pivot about the longitudinal axis of the threaded shaft 160, and the spinal rod 12 is permitted to slide, and rotate, within slot 142 of inner housing 130. Using the partially locked configuration of the bone screw 80, the clinician can first position the bone screw 80 relative to the bone (e.g., vertebra "V") into which the threaded shaft 160 has been attached and then manipulate the dual layered housing 200 relative to the screw head 130, and further manipulate the spinal rod 12 relative to the slot 142. Thus, the clinician may optimize the position of the bone screw 80 and spinal rod 12 before sliding the outer housing 120 relative to the inner housing 140 and placing the dual layered housing 200 in the fully locked configuration (FIG. 10B).

With reference to FIGS. 4 and 5, shaft 50 has threads thereon and includes a distal portion 54 with an annular groove 52 and a head 58 with a recess 59. It is envisioned that recess 59 may be configured to cooperatively engage any number of driving tools known in the art to effect torque driven rotation. For example, recess 59 may be configured as a hex socket (FIG. 4), a hex head, a Philips head, or a slotted head. Anvil 40 defines a cavity 42, an aperture 46, pin holes 48, and a receiving saddle 49. Aperture 46 is configured to receive the distal portion 54 of shaft 50 therein, and receiving saddle 49 is configured to engage an outer surface of spinal rod 12. It is contemplated that receiving saddle 49 may be configured to accommodate a range of spinal rod 12 diameters and cross-sections. For example, receiving saddle 49 may be adapted to cooperatively engage a spinal rod 12 having a variance in diameter of between about 3 mm to about 8 mm, while still delivering the necessary driving force to secure the spinal rod 12 into bone screw 80. Receiving saddle 49 may be generally arched or convex, but may take the form of any geometric shape adapted to cooperatively engage with and drive a spinal rod during reduction.

Each locking foot 70 includes pin holes 72 disposed at a proximal end 71, pin holes 74 disposed at a position distal of proximal end 71, and an engagement surface 76 disposed at a distal end 75 on an inner facing surface. As discussed further herein, engagement surface 76 is configured to engage with outer housing 120 of dual layered housing 200. It is contemplated that engagement surface 76 may define, for example, a lip, ridge, hook, or any suitable feature to engage a corresponding feature of outer housing 120 such as, for example, annular ridge, lip, or flange 122.

Shaft 50 is coupled to anvil 40 such that proximal and distal movement of shaft 50 results in a corresponding proximal and distal movement of anvil 40. The distal portion 54 of shaft 50 is insertable through aperture 46 of anvil 40, where pins 44 pass through pin holes 48 of anvil 40 and pin holes 74 of locking feet, such that a portion of each pin 44 resides in the annular groove 52 at the distal end 54 of shaft 50. Pins 44 are used to maintain the shaft 50 within the anvil 40, and couple shaft 50, through anvil 40, to locking feet 70.

Housing 20 includes a throughhole 26 which defines a longitudinal axis "L" (as seen in FIG. 5). At least a portion of throughhole 26 has threads that are complementary to threads disposed on an outer surface of shaft 50. It is envisioned that throughhole 26 may be elongated, oval, or any suitable cross-section such that shaft 50 may be inserted and rotatably retained therein. Additionally, it is envisioned that throughhole 26 has a diameter which is larger than a diameter of shaft 50. Each arm member 30 is pivotably coupled at a proximal end 31 thereof to housing 20 such that arm members 30 are capable of pivoting with respect to the longitudinal axis "L" of housing 20. In one embodiment, arm members 30 are pinned in place relative to housing 20 with pins 32 extending from proximal ends 31 of arm members 30. It is contemplated that distinct pins may be used to couple arm members 30 to housing 20. It is further envisioned that arm members 30 may be integrally formed with housing 20 such that, rather than pivoting relative to housing 20, arm members 30 flex relative to housing 20. In such an embodiment, pins 32 may be omitted and arms 30 may be directly attached to housing 20. Pins 32 extend through pin holes 22 of the housing 20. Pin holes 22 in combination with pins 32 define a pivot axis for arm members 30. Each arm member 30 further defines a hooked portion 34 at a distal end 35. As discussed further herein, each hooked portion 34 is configured to engage inner housing 140 of dual layered housing 200, as illustrated in FIGS. 6A-8B. Additionally, each arm member 30 is insertable through a respective cavity 42 of the anvil 40, such that the hooked portions 34 are positioned distal of anvil 40.

It should be appreciated that with each arm member 30 disposed in a respective cavity 42 of anvil 40, as anvil 40 moves distally as a result of distal movement of shaft 50 (e.g., rotation of shaft 50 in a first direction), arm members 30 pivot with respect to housing 20 about pin holes 22 and pins 32 towards a parallel configuration or substantially parallel configuration. Conversely, as anvil 40 moves proximally as a result of proximal movement of shaft 50 (e.g., rotation of shaft 50 in a second direction), arm members 30 are capable of pivoting outwards out of the parallel configuration. In an alternate embodiment, as anvil 40 is translated distally with respect to housing 20, each arm member 30 flexes relative to housing 20 such that the arm members 30 are urged into a parallel configuration. With anvil 40 in a proximal most position, arm members 30 are in a first configuration, and may be engaged or disengaged with inner housing 140 of dual layered housing 200 (FIG. 6A). With anvil 40 in a distal most position, arm members 30 are in a second configuration, and are configured to be securely engaged with inner housing 140 of dual layered housing 200 (FIGS. 7A-8B). During reduction of spinal rod 12, anvil 40 travels distally with respect to housing 20 from the proximal most position to the distal most position, and arm members 30 move from the first configuration towards the second or parallel configuration. As arm members 30 move towards the parallel configuration, hooked portions 34 of arm members 30 engage the inner housing 140 of dual layered housing 200. As spinal rod 12 is reduced towards and into dual layered housing 200, the engagement of hooked portions 34 to inner housing 140 serves to maintain alignment of rod reducer 100 with respect to the dual layered housing 200.

Figure 3:
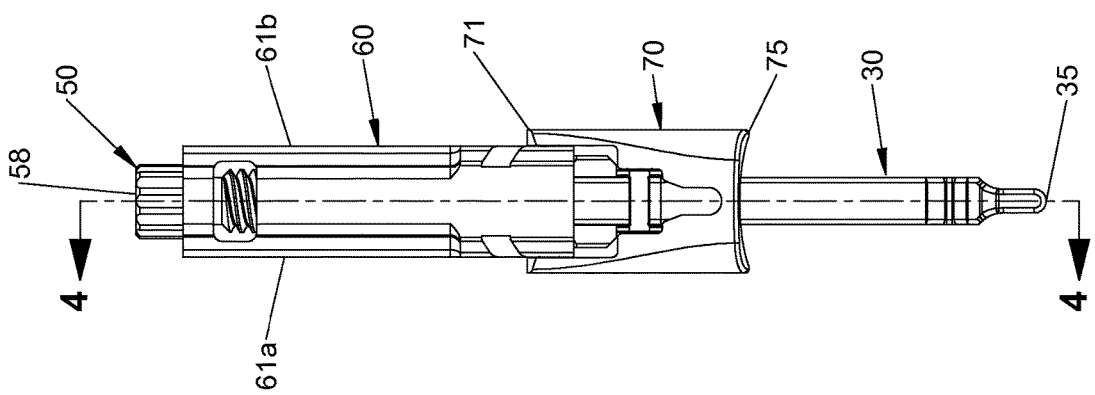
FIG. 3 is a side view of the rod reducer of FIG. 1.

With reference to FIG. 5, sleeve 60 defines a longitudinal cavity 64 disposed about a longitudinal axis "S", where the cavity 64 is configured to slidably receive housing 20 therein such that the longitudinal axis "L" of housing 20 and the longitudinal axis "S" of sleeve 60 are coaxial. Sleeve 60 further defines cam slots 62 where each cam slot 62 has a first end 62a and a second end 62b. Cam slots 62 are disposed on opposing surfaces 61a, 61b (FIG. 3) of sleeve 60, and are symmetrical about the longitudinal axis "S". Cam slots 62 are configured such that first ends 62a are distal of second ends 62b, and further, an axis "C" of cam slots 62 define an angle θ with respect to the longitudinal axis "S" (FIG. 1). It is contemplated that an acute angle θ may be formed between the axis "C" of cam slots 62 and the longitudinal axis "S" of sleeve 60, where the second end 62b of each cam slot 62 is spaced away from the longitudinal axis "S". Sleeve 60 is coupled to locking feet 70 with pins 66, which pass through pin holes 72 of locking feet 70 and into cam slots 62. It should be appreciated that pins 66 slide within cam slots 62 between the first and second ends 62a, 62b as a result of proximal or distal translation of sleeve 60 with respect to anvil 40. As pins 66 translate between the first ends 62a and the second ends 62b, locking feet 70 pivot with respect to the longitudinal axis "S" of sleeve 60 about pin holes 74 of the locking feet 70, pin holes 48 of anvil 40, and pins 44.

Figure 8C:
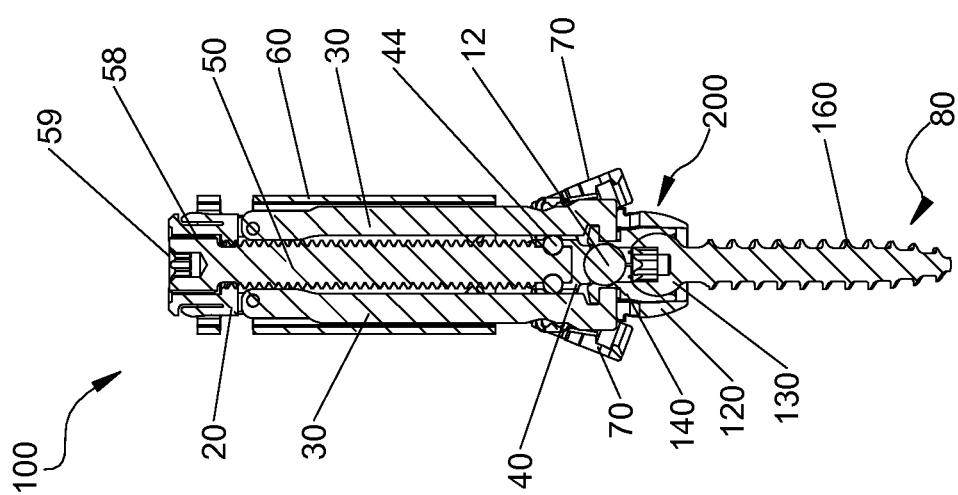
FIG. 8C is a cross-sectional view taken along section line 8C-8C of FIG. 8B.

More specifically, with sleeve 60 in a proximal most position with respect anvil 40, pins 66 are positioned in approximation to the first ends 62a of cam slots 62, and locking feet 70 are in a spaced apart position with respect to one another (FIGS. 6A-7B). With sleeve 60 in a distal most position with respect to anvil 40, pins 66 are positioned in approximation to the second ends 62b of cam slots 62, and locking feet 60 are in a parallel or substantially parallel relationship with one another (FIGS. 8A and 8B). Accordingly, as sleeve 60 is manually translated between the proximal most position and the distal most position, with respect to anvil 40, locking feet 70 pivot between a spaced apart position and a parallel relationship, with respect to one another. As indicated by arrow "A" of FIG. 8A, proximal and distal translation of sleeve 60 with respect to anvil 40 transitions pins 66 between the first and second ends 62a, 62b of cam slot 62, respectively. With pins 66 near the first ends 62a of cam slots 62, locking feet 70 are in a released configuration and are couplable to outer housing 120 of dual layered housing 200, and with pins 66 near the second ends 62b of cam slots 62, locking feet 70 are in an engaged configuration and are securely coupled to outer housing 120. As such, locking feet 70 pivot into, and out of, the engaged and released configurations. It should be appreciated that as sleeve 60 translates proximally, towards the proximal most position with respect to anvil 40, the distal ends 75 of locking feet 70 pivot towards one another such that a force is exerted therebetween, i.e., when coupled to outer housing 120, such that locking feet 70 exert a compressive force radially inward upon the outer surface of outer housing 120.

It should be appreciated that a limit of proximal and distal translation of sleeve 60 relative to anvil 40 may be governed by pins 66 abutting the first or second ends 62a, 62b of cam slots 62. Alternatively, the limit of proximal and distal translation of sleeve 60 relative to anvil 40 may be governed by locking feet 70 coming into abutment with the outer housing 120 of dual layered housing 200 when in the engaged configuration, which may thus inhibit pins 66 from translating further within cam slot 62 and thus inhibit further translation of sleeve 60. Further, sleeve 60 may be manually retained in, or biased into, one of the proximal most position, distal most position, or a position therebetween during use, as described herein.

As referenced above, shaft 50, anvil 40, and locking feet 70 are coupled together, such that clockwise and counter-clockwise rotation of shaft 50 translates anvil 40 with respect to housing 20 in a first and a second direction (e.g., proximally and distally) and simultaneously translates locking feet 70 in the first or second direction. For example, rotation of shaft 50 in a first direction (e.g., clockwise) results in translation of anvil 40 in a first direction (e.g., proximally), which results in translation of locking feet 70 in the first direction. With sleeve 60 translated into the distal most position with respect to anvil 40, locking feet 70 are in the engaged configuration and securely coupled to outer housing 120. Thus, rotation of shaft 50 in the first direction translates anvil 40 in the first direction and translates locking feet 70 in the first direction resulting in outer housing 120 translating proximally with respect to inner housing 140. As noted above, the translation of outer housing 120 proximally with respect to inner housing 140 of dual layered housing 200 transitions dual layered housing 200 from the unlocked configuration into the partially locked configuration or the locked configuration. The transition of dual layered housing 200 is governed by the amount of proximal translation of outer housing 120 with respect to inner housing 140, and thus it should be appreciated that the transition of dual layered housing 200 is determined by the proximal translation of anvil 40, and more directly, the proximal translation of locking feet 70 which are coupled to outer housing 120. It should be appreciated that notches 126 (FIG. 6B) defined on annular flanges 122 of outer housing 120 are configured to receive the distal ends 35 of arm members 30 therein. Accordingly, as outer housing 120 is driven proximally with respect to inner housing 140, arm members 30 coupled to inner housing 140 may be received in notches 126, thus allowing clearance between arm members 30 and outer housing 120.

A method of using rod reducer 100 in accordance with the present disclosure is described with reference to FIGS. 1-9. Further, the method described herein may be performed with a plurality of bone screws 80, rod reducers 100, and one or more spinal rods 12. The bone screws 80 may be implanted in a number of vertebrae "V" (FIG. 9), to facilitate the reduction of spinal rod 12 into a plurality of dual layered housings 200 such that spinal rod 12 spans multiple levels of vertebrae (FIG. 9). The clinician may perform the method described herein to facilitate the reduction of the plurality of spinal rods 12 into the plurality of dual layered housings 200 to a number of vertebrae in sequence. It is further envisioned that the clinician may be provided with multiple spinal rods 12 of varying sizes that may range between about 3 mm and about 8 mm.

A spinal rod and screw construct is assembled in a patient as follows. A clinician implants the bone screw 80 into a spinal vertebra "V" with dual layered housing 200 positioned in the unlocked configuration to receive spinal rod 12 therein. It is envisioned that a clinician may implant a plurality of bone screws 80 in sequence into several vertebrae "V" during a procedure. Once the desired number of bone screws 80 have been implanted, the clinician aligns and manipulates the spinal rod 12 such that a portion of the spinal rod 12 is approximated to the slot 142 of inner housing 140 of the dual layered housing 200 of each respective bone screw 80, such that spinal rod 12 creates an unbroken connection between each implanted bone screw 80.

The clinician positions rod reducer 100 into proximity with each implanted bone screw 80, such that hooked portions 34 of arm members 30 abut to the inner housing 140 of each respective bone screw 80 (FIGS. 6A and 6B). Next, rotation of shaft 50 in a first direction results in distal translation of anvil 40 causing arm members 30 to pivot into the second position such that hooked portions 34 grasp, clip, or are otherwise affixed to the inner housing 140. During reduction of spinal rod 12, attachment of rod reducer 100 to the bone screw 80, and alignment of spinal rod 12 to the dual layered housing 200, is maintained. Spinal rod 12 is positioned between the dual layered housing 200, the anvil 40, and the arm members 30, and may be in abutment with the receiving saddle 49 of anvil 40 (FIGS. 6A and 6B) or in abutment with the slot 142 of the inner housing 140 of the dual layered housing 200 (FIG. 10B).

The clinician next actuates the rod reducer 100 and reduces spinal rod 12 into slot 142 of the inner housing 140 of the dual layered housing 200 by continuing to rotate shaft 50 manually, or with a surgical tool (not shown) as is known in the art, such that anvil 40 translates distally with respect to dual layered housing 200. Saddle 49 of anvil 40 contacts an outer surface of spinal rod 12 and urges spinal rod 12 into the slot 142 of inner housing 140 as anvil 40 moves distally. As spinal rod 12 is being reduced distally towards dual layered housing 200 and urged into the slot 142 of inner housing 140, sleeve 60 is in the proximal most position with respect to anvil 40 such that locking feet 70 are positioned in the released configuration. Once spinal rod 12 is reduced into dual layered housing 200, sleeve 60 may be manually translated distally by the clinician into the distal most position with respect to anvil 40, such that locking feet 70 pivot into the engaged configuration, coupling engagement surface 76 of locking feet 70 to the annular flange 122 of outer housing 120. With a plurality of rod reducers 100, where each rod reducer 100 is mounted to a respective bone screw 80, the clinician is able to gradually reduce the spinal rod 12 towards the inserted bone screws 80 by sequentially actuating each rod reducer 100 until all rod reducers 100 have been actuated and the spinal rod 12 is reduced into all of the bone screws 80 (FIG. 9).

With the rod reducer 100 attached to bone screw 80, it is envisioned that the clinician may additionally use rod reducer 100 to further assist the alignment of spinal rod 12 between multiple bone screws 80. The rod reducer 100 provides a mechanical advantage to further bend or shape spinal rod 12 while spinal rod 12 is securely held by rod reducer 100 and dual layered housing 200. In this configuration, the clinician may make final adjustments to the spinal rod 12 when connecting spinal rod 12 between multiple bone screws 80. It is also envisioned that additional tools, as are known in the art, may be coupled to the rod reducers 100 to assist in manipulating the spinal rod 12 into a desired configuration for the construct. After spinal rod 12 is properly aligned, the clinician locks the respective bone screws 80 by rotating shaft 50 in a second direction, being opposite from the first direction, such that anvil 40, and locking feet 70 coupled therewith, are translated proximally. During proximal movement of locking feet 70, outer housing 120 is translated proximally relative to inner housing 140 thereby transitioning each bone screw 80 from an unlocked configuration to either a partially locked configuration or a locked configuration. It is contemplated that the clinician may partially lock one or more bone screws 80, make additional adjustments to the spinal rod 12 or bone screws 80 before transitioning the bone screws from the partially locked configuration to the locked configuration. It is further envisioned that the clinician may manually retain sleeve 60 in the distal most position as the shaft 50 is rotated in the second direction. This final locking of the spinal rod 12 may be performed using the rod reducer 100 or may be accomplished using another locking tool (not shown) as is known in the art. An example of a suitable tool for locking bone screw 80 is disclosed in U.S. Pat. No. 8,361,122, which is hereby incorporated by reference in its entirety.

In particular, transitioning the bone screw 80 from the unlocked configuration to either the partially locked or locked configuration is accomplished by rotating shaft 50 in the first direction which results in distal translation of the anvil 40. As anvil 40 is reduced distally and brought in approximation with dual layered housing 200, sleeve 60 is positioned in the proximal most position with respect to anvil 40 such that pins 66 are positioned in approximation with the first ends 62a of cam slots 62 and locking feet 70 are in the released configuration such that the engagement surfaces 76 may be coupled to the annular flange 122 of outer housing 120. Once anvil 40 is fully reduced and spinal rod 12 is reduced into slot 142 of inner housing 140 of dual layered housing 200, sleeve 60 is translated distally into the distal most position with respect to anvil 40 such that pins 66 slide towards, and into approximation with, the second ends 62b of cam slots 62 and locking feet 70 pivot into the engaged configuration such that the engagement surfaces 76 come into abutment with, and exert a compressive force radially inward upon, outer housing 122, and more specifically annular flange 122 of outer housing 120, thus coupling locking feet 70 and outer housing 120. Once coupled, shaft 50 is rotated in the second direction, opposite the first direction, such that anvil 40, and locking feet 70 coupled therewith, translate proximally. Proximal translation of locking feet 70 translate outer housing 120 proximally with respect to inner housing 140, such that dual layered housing 200 transitions from the unlocked configuration into the partially locked configuration. With dual layered housing 200 in the partially locked configuration, spinal rod 12 is maintained therein such that the clinician may perform fine adjustments to spinal rod 12 and dual layered housing 200. The clinician may slide spinal rod 12 within slot 142 of inner housing 140 in a direction transverse to the longitudinal axis "H" of dual layered housing 200, or adjust the rotational and pivotal position of dual layered housing 200 with respect to threaded shaft 160, as described above. Once final adjustments have been made, the clinician may further rotate shaft 50 in the second direction such that anvil 40 and locking feet 70 continue to translate proximally to drive outer housing 120 proximally with respect to inner housing 140, transitioning dual layered housing 200 into the locked configuration.

To decouple rod reducer 100 from the bone screw 80, the clinician translates sleeve 60 proximally into the proximal most position with respect to anvil 40 such that locking feet 70 pivot into the released configuration and may be decoupled from outer housing 120. With locking feet 70 decoupled, shaft 50 may be further rotated in the second direction such that anvil 40 may be translated proximally, where proximal translation of anvil 40 allows arm members 30 to pivot into the first position which facilitates the hooked portions 34 of arm members 30 to be decoupled from the inner housing 140. With the arm members 30 decoupled from inner housing 140, rod reducer 100 may be decoupled from bone screw 80.

In accordance with the present disclosure, a kit will be described with reference to FIGS. 1-10. The kit includes one or more rod reducers 100. The kit may further include bone screws 80, spinal rods 12, an orthopedic tool or device (not shown), and instructions for use. Examples of the orthopedic tool or device may be a tightening or loosening tool, a locking or unlocking tool, or an alignment tube. Further, the kit may include bone screws 80, and/or spinal rods 12, having a variety of sizes and dimensions. The kit may include a thermoformed plastic tray and/or other packaging materials within the view of those skilled in the art.

It is further contemplated that sleeve 60 and locking feet 70, and the method of use and kit provided herein, may be adapted for use with a variety of rod reducer devices. For a detailed description and illustration of rod reducer devices reference may be made to U.S. Patent Application Publication No. 2015/0100097, filed Oct. 7, 2014, and U.S. Patent Application Publication No. 2015/0100098, filed Oct. 7, 2014, the entire contents of each of which are hereby incorporated by reference in their entirety.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus, the scope of the embodiments should be determined by the claims of the present application and their legal equivalents, rather than by the examples given.

What is claimed is:

1. A surgical apparatus comprising:
a bone screw having inner and outer housings movable relative to each other between partially locked and unlocked configurations; and
a rod reducer including:
a sleeve having a housing slidably disposed therein;
a shaft disposed through a longitudinal opening of the housing;
an anvil coupled to a distal end of the shaft, rotation of the shaft in a first direction translates the anvil proximally relative to the housing and rotation of the shaft in a second direction translates the anvil distally relative to the housing;
first and second arm members operatively coupled to the anvil and the housing, the first and second arm members pivotable relative to the housing with the anvil in a proximal position, the first and second arm members in a parallel arrangement with the anvil in a distal position; and
first and second locking feet slidably coupled at proximal ends thereof to the sleeve and pivotably coupled with the anvil, such that the first and second locking feet are pivotable between a released configuration and an engaged configuration, wherein proximal translation of the sleeve with respect to the anvil pivots the first and second locking feet towards the released configuration and distal translation of the sleeve with respect to the anvil pivots the first and second locking feet towards the engaged configuration such that the first and second locking feet pivot towards a parallel relationship.

2. The surgical apparatus of claim 1, wherein the bone screw includes a head and a shank, the head disposed in the inner housing such that the shank is rotatable and pivotable relative to the inner housing.

3. The surgical apparatus of claim 1, wherein pins couple the first and second locking feet to cam slots of the sleeve, such that the pins move towards first ends of the cam slots in the released configuration and the pins move towards second ends of the cam slots in the engaged configuration.

4. The surgical apparatus of claim 3, wherein proximal translation of the sleeve slides the pins towards the first ends of the cam slots.

5. The surgical apparatus of claim 3, wherein distal translation of the sleeve slides the pins towards the second ends of the cam slots.

6. The surgical apparatus of claim 1, wherein the distal ends of the first and second locking feet are configured to engage with an annular flange extending from a proximal end of the outer housing.

7. The surgical apparatus of claim 1, wherein proximal translation of the sleeve pivots the first and second locking feet towards the released configuration.

8. The surgical apparatus of claim 1, wherein the first and second locking feet define an acute angle with respect to a longitudinal axis of the shaft in the released configuration.

9. A method of reducing a spinal rod comprising:
coupling a first arm member and a second arm member of a rod reducer with an inner housing of a bone screw, the first and second arm members pivotably coupled to a housing of the rod reducer;
positioning a spinal rod between an anvil of the rod reducer and the inner housing;
translating a sleeve of the rod reducer distally with respect to the anvil, such that locking feet pivotably coupled to the anvil and slidably coupled to the sleeve transition towards a parallel orientation with respect to each other;
coupling a distal end of each locking foot to an outer housing of the bone screw;
translating the anvil and the locking feet proximally with respect to the housing such that the bone screw transitions from an unlocked configuration to a partially locked configuration.

10. The method of claim 9, wherein translating the anvil distally includes rotating a shaft coupled to the anvil in a first direction.

11. The method of claim 10, wherein translating the anvil proximally includes rotating the shaft in a second direction.

12. The method of claim 9, wherein translating the sleeve distally further includes sliding pins disposed within cam slots of the sleeve from first ends of the cam slots towards second ends of the cam slots such that the locking feet are in the parallel orientation when the pins are approximated to the second ends of the cam slots.

13. The method of claim 9, further comprising:
translating the sleeve proximally with respect to the anvil, such that the locking feet transition into a spaced apart orientation with respect to one another;
decoupling the locking feet from the outer housing of the bone screw;
translating the anvil proximally; and
decoupling the first and second arm members from the inner housing of the bone screw.

14. The method of claim 9, wherein translating the anvil proximally includes rotating a shaft coupled to the anvil in a first direction.

15. The method of claim 14, wherein translating the anvil distally includes rotating the shaft in a second direction.

16. A kit comprising:
at least one rod reducer including,
a housing slidably disposed in a sleeve;
a shaft disposed in a throughhole of the housing and coupled to an anvil;
locking feet pivotably coupled to the anvil and slidably coupled to the sleeve, the locking feet attachable to an outer housing of a bone screw in a released configuration and securely attached to the outer housing in an engaged configuration, wherein distal translation of the sleeve with respect to the anvil pivots the locking feet towards the engaged configuration; and
first and second arm members pivotably coupled to the housing and configured to engage an inner housing of the bone screw;
at least one bone screw; and
at least one spinal rod.

17. A rod reducer comprising:
a sleeve having a housing slidably disposed therein;
a shaft disposed through a longitudinal opening of the housing;
an anvil coupled to a distal end of the shaft, the shaft rotatable in a first direction to translate the anvil proximally relative to the housing and the shaft rotatable in a second direction to translate the anvil distally relative to the housing;
first and second arm members operatively coupled to the anvil and the housing, the first and second arm members pivotable relative to the housing with the anvil in a proximal position, the first and second arm members parallel to each other with the anvil in a distal position; and
first and second locking feet slidably coupled at proximal ends thereof to the sleeve and pivotably coupled with the anvil, such that the first and second locking feet are pivotable between a released configuration and an engaged configuration, wherein proximal translation of the sleeve with respect to the anvil pivots the first and second locking feet towards the released configuration and distal translation of the sleeve with respect to the anvil pivots the first and second locking feet towards the engaged configuration such that the first and second locking feet pivot towards a parallel relationship.

* * * * *